United States Patent [19]
Kishino et al.

[11] 3,970,728
[45] July 20, 1976

[54] O-ARYL-ALKOXYETHYL-THIOLPHOSPHORIC ACID ESTER

[75] Inventors: Shigeo Kishino, Tokyo; Akio Kudamatsu, Kanagawa; Shozo Sumi, Tokyo; Kozo Shiokawa, Kanagawa, all of Japan

[73] Assignee: Bayer Aktiengesellschaft, Leverkusen, Germany

[22] Filed: Mar. 29, 1974

[21] Appl. No.: 456,481

Related U.S. Application Data

[62] Division of Ser. No. 298,911, Oct. 19, 1972, Pat. No. 3,822,328.

[30] Foreign Application Priority Data

Oct. 21, 1971   Japan.............................. 46-83487

[52] U.S. Cl................................. 260/949; 260/941; 260/951
[51] Int. Cl.².......................... C07F 9/24; A01N 9/36
[58] Field of Search.................... 260/949, 951, 941

[56] References Cited
UNITED STATES PATENTS 3,798,292   3/1974   Kishino et al..................... 260/949 X

*Primary Examiner*—Anton H. Sutto
*Attorney, Agent, or Firm*—Burgess, Dinklage & Sprung

[57] ABSTRACT

O-aryl-alkoxyethyl-thiolphosphoric acid ester amides of the formula

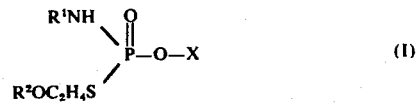

in which
R$^1$ is hydrogen or lower alkyl,
R$^2$ is lower alkyl, and
X is a group of the formula

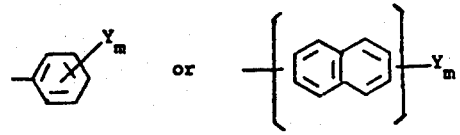

in which
m is 0, 1, 2 or 3, and
each Y independently is halogen, lower alkyl, lower alkoxy, lower alkylmercapto, lower alkoxycarbonyl, nitro or phenyl,
which possess insecticidal, acaricidal and nematocidal properties.

10 Claims, No Drawings

O-ARYL-ALKOXYETHYL-THIOLPHOSPHORIC ACID ESTER AMIDES

This is a division, of application Ser. No. 298,911, filed Oct. 19, 1972, now U.S. Pat. No. 3,822,328, issued July 2, 1974.

The present invention relates to and has for its objects the provision of particular new O-aryl-S-alkoxyethylthiolphosphoric acid ester amides which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g., insects, acarids and nematodes, with other and further objects becoming apparent from a study of the within specification and accompanying examples.

It has been disclosed in Japanese Patent Publication No. 15261/61 that the compound (A) of the formula $$\begin{array}{c} CH_3NH \\ \diagdown \\ C_2H_5SC_2H_4 \end{array} \!\!\!\!\! P \!\!\!\! \begin{array}{c} O \\ \diagup \\ OC_2H_5 \end{array}$$

has insecticidal activity.

The present invention provides, as new compounds, the thiophosphoric acid ester amides of the general formula $$\begin{array}{c} R^1NH \\ \diagdown \\ R^2OC_2H_4S \end{array} \!\!\!\!\! P \!\!\!\! \begin{array}{c} O \\ \diagup \\ O-X \end{array} \qquad (I)$$

in which
R$^1$ is hydrogen or lower alkyl,
R$^2$ is lower alkyl, and
X is a group of the formula <chemical structure: phenyl with Y_m substituents, or naphthyl with Y_m substituents> in which
m is 0, 1, 2 or 3, and
each Y independently is lower alkyl, lower alkoxy, lower alkylmercapto, lower alkoxycarbonyl, nitro or phenyl.

Preferably, the lower alkyl moieties of the lower alkyl, alkoxy, alkylmercapto and alkoxycarbonyl groups have 1 to 4 carbon atoms.

It has been found that the novel thiolphosphoric acid ester amides of the general formula (I) have excellent insecticidal, acaridical and nematodical activities. They are superior to the chemically similar compound (A) and to other compounds having similar activities.

Compared with active compounds with similar structures which have been described in the literature or known compounds exhibiting similar activities, the compounds of this invention exhibit substantially improved effects and have a very low toxicity to warm-blooded animals. Accordingly, the compounds of this invention are of great utility.

The present invention also provides a process for the preparation of a compound of the formula (I) above, in which an amido-thiophosphoric acid salt of the general formula $$\left[ \begin{array}{c} R^1NH \\ \diagdown \\ X-O \end{array} \!\!\!\!\! P \!\!\!\! \begin{array}{c} S \\ \diagup \\ O \end{array} \right] \cdot M \qquad (II)$$

in which
R$^1$ and X have the meanings stated above, and
M is a metal (preferably sodium or potassium) atom or an ammonium group,
is reacted with a 2-alkoxyethyl halide of the general formula $$Hal\text{-}C_2H_4OR^2 \qquad (III),$$

in which
R$^2$ has the meaning stated above, and
Hal is halogen, preferably chlorine, bromine or iodine.

Examples of the amido-thiophosphoric acid salts of the general formula (II) are the potassium, sodium and ammonium salts of N-methyl(or iso-propyl)-O-phenyl-amido-thiophosphoric acid, N-methyl (or sec.-butyl)-O-chlorophenyl-amido-thiophosphoric acid, N-isopropyl-O-2(or 3 or 4)-chlorophenyl-amido-thiophosphoric acid, N-methyl(or ethyl, isopropyl or sec.-butyl)-O-(2,4-dichlorophenyl)-amido-thiophosphoric acid, N-isopropyl-O-(2,6-dichlorophenyl)-amido-thiophosphoric acid, N-methyl(or isopropyl)-O-(2,4,5-trichlorophenyl)-amido-thiophosphoric acid, N-ethyl(or isopropyl)-O-(2,4,6-trichlorophenyl)-amido-thiophosphoric acid, N-methyl(or isopropyl)-O-(4-bromophenyl)-amido-thiophosphoric acid, N-isopropyl-O-(2(or 3 or 4)-methylphenyl-amido-thiophosphoric acid, N-methyl(or isopropyl)-O-(2-isopropylphenyl)-amido-thiophosphoric acid, N-methyl(or isopropyl, n-butyl or sec.-butyl)-O-(tert.-butylphenyl)-amido-thiophosphoric acid, N-methyl(or isopropyl)-O-2,4(or 3,4 or 3,5)-dimethylphenyl-amido-thiophosphoric acid, N-methyl(or isopropyl)-O-(2-isopropyl-5-methylphenyl)-amido-thiophosphoric acid, N-isopropyl-O-(3-methyl-4-chlorophenyl)-amido-thiophosphoric acid, N-isopropyl-O-(2-chloro-4-methylphenyl)-amido-thiophosphoric acid, N-isopropyl(or sec.-butyl)-O-(3,5-dimethyl-4-chlorophenyl)-amido-thiophosphoric acid, N-isopropyl-O-(2,4-dichloro-6-methylphenyl)-amido-thiophosphoric acid, N-methyl(or isopropyl)-O-(2-chloro-4-tert.-butylphenyl)-amido-thiophosphoric acid, N-methyl-O-(2,6-dichloro-4-tert.-butylphenyl)-amido-thiophosphoric acid, N-methyl(or isopropyl)-O-2(or 4)-methoxyphenyl-amido-thiophosphoric acid, N-methyl(or isopropyl)-O-(4-methylphenyl)-amido-thiophosphoric acid, N-methyl(or isopropyl)-O-(4-methylthiophenyl)-amido-thiophosphoric acid, N-methyl(isopropyl)-O-(3-methyl-4-methylthiophenyl)-amido-thiophosphoric acid, N-isopropyl-O-(2-methyl-4-methylthiophenyl)-amido-thiophosphoric acid, N-isopropyl-O-(3,5-dimethyl-4-methylthiophenyl)-amido-thiophosphoric acid, N-methyl(or isopropyl or sec.-butyl)-O-4(or 2)-nitrophenyl-amido-thiophosphoric acid, N-methyl(or isopropyl)-O-(2-nitro-4-methylphenyl)-amido-thiophosphoric acid, N-isopropyl-O-(2-chloro-4-nitrophenyl)-amido-thiophosphoric acid, N-isopropyl-O-(3-methyl-4-nitrophenyl)-amido-thiophosphoric acid, N-methyl(or isopropyl)-O-2(or 4)-biphenyl-amido-thiophosphoric acid, N-isopropyl-O-(4-methoxycarbonylphenyl)-amido-thiophosphoric acid, N-methyl(or isopropyl)-O-αO-(β)-naphthyl-amido-thiophosphoric acid, O-(4-chlorophenyl)-amido-thiophosphoric acid, O-(2,4-dichlorophenyl)-amido-thiophosphoric acid, O-(2-isopropylphenyl)-amido-thiophosphoric acid and O-(4-tert.-butylphenyl)-amido-thiophosphoric acid.

Examples of the 2-alkoxyethyl halides of the general formula (III) are 2-methoxyethyl chloride, 2-methoxyethyl bromide, 2-methoxyethyl iodide, 2-n-propoxyethyl chloride, 2-n-propoxyethyl bromide, 2-n-propoxyethyl iodide, 2-isopropoxyethyl chloride, 2-isopropoxyethyl bromide, 2-isopropoxyethyl iodide, 2-ethoxyethyl chloride, 2-ethoxyethyl bromide, 2-ethoxyethyl iodide, 2-n-butoxyethyl chloride, 2-n-butoxyethyl bromide and 2-n-butoxyethyl iodide.

In the synthesis of the active compounds of this invention according to the above process, the reaction is preferably carried out in a solvent or diluent. For this purpose, any inert solvent or diluent may be used, especially water or an inert organic solvent such as an aliphatic, alicyclic or aromatic hydrocarbon (which may be chlorinated), for example hexane, cyclohexane, petroleum ether, ligroin, benzene, toluene, xylene, methylene chloride, chloroform, carbon tetrachloride, ethylenchloride, tri-chloroethylene or chlorobenzene; an ether, for example diethyl ether, methyl ethyl ether, di-isopropyl ether, dibutyl ether, ethylene oxide, dioxane or tetrahydrofuran; a ketone such as acetone, methyl ethyl ketone, methyl isopropyl ketone or methyl isobutyl ketone; an alcohol such as methanol, isopropanol, butanol or ethylene glycol; a nitrile such as acetonitrile, propionitrile or acrylonitrile; an ester such as ethyl acetate or amyl acetate; an acid amide such as dimethyl formamide or dimethyl acetamide; or a sulfone or sulfoxide such as dimethyl sulfoxide or sulfolane.

The reaction may be effected at temperatures within a fairly broad range, but generally, the reaction is carried out at about −20°C to the boiling point of the reaction mixture, preferably at about 0° to 100°C or to the boiling point of the reaction mixture, whichever is the lower. It is preferable to carry out the reaction under atmospheric pressure, although it is possible to conduct the reaction under reduced or elevated pressure.

The preparative process of the present invention may be illustrated by the following equation:

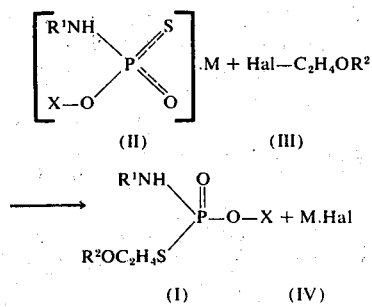

wherein
R¹, R², X, M and Hal have the meanings stated above.

The amido-thiophosphoric acid salts of the general formula (II) to be used as starting materials may be synthesized by conventional methods. For instance, they may be synthesized by reacting suitable N-alkyl-O-substituted (or unsubstituted) phenyl (or naphthyl) amido-thiono-phosphoric acid chlorides (V) with an alkali (VI), according to the following reaction:

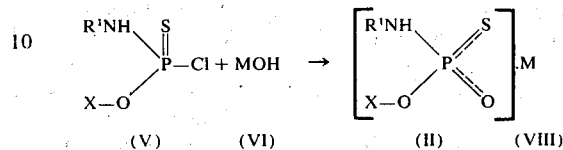

wherein R¹, X and M are as defined above. The resulting amido-thiophosphoric acid salts may be used after isolation, or they may be directly reacted in situ with the 2-alkoxyethyl halides of the general formula (III).

The compounds of formula (I) have an excellent insect-killing property and can be utilized for controlling various harmful insects such as sucking insects, biting insects, plant parasites, insects destructive of stored grain and insects harmful to health.

For instance, compounds of formula (I) are effective for controlling insects belonging to the Coleoptera such as *Sitophilus oryzae*, *Tribolium castaneim*, *Epilachna vigintioctomaculata*, *Agriotes fuscicollis* and *Anomola rufocuprea*; insects belonging to the Lepidoptera such as *Lymantria dispar*, *Malacosoma neustria*, *Pieris brassicae*, *Prodenia litura*, *Chilo suppressalis*, *Adoxophyes orana* and *Ephestia cautella*; insects belonging to the Hemiptera such as *Nephotettix cincticeps*, *Nilaparvata lugens*, *Pseudococcus comstocki*, *Unaspis yanonensis*, *Myzus persicae*, *Aphis pomi* and *Brevicoryne brassicae*; insects belonging to the Orthoptera such as *Blattella germanica*, *Periplaneta americana* and *Gryllotalpa africana*; and insects belonging to the Isoptera such as *Musca domestica*, *Aedes aegypti*, *Hylemia platura*, *Culex pipiens*, *Anopheles sinensis* and *Culex tritaeniorhynchus*. The compounds are also active against mites, such as *Tetranychus urticae*, *Panonychus citri* and *Aculus pelekassi*, and against nematodes, such as *Meloidogyne incognita acrita*, *Aphelenchoides besseyi* and *Heterodera glycines*.

In the veterinary field, compounds of this invention are effective as agents for controlling various animal parasites (endoparasites and ectoparasites), for instance certain spiders and helminths.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Possible adjuvants include organic matter; stabilizer; adhesive agents, for example, soap, calcium caseinate, sodium alginate, polyvinyl alcohol, steeping agents, coumarone (or indene) resins or polyvinyl butyl ether; combustible materials (for fumigants), for example, nitrites, zinc dust or dicyandiamide; oxygen-yielding substances, for example, perchlorates or dichromates; phytotoxicity-reducing substances, for example, zinc sulfate, ferrous chloride or copper nitrate; substances for prolonging the biological effect, for example, chlorinated terphenyls; emulsion-stabilizing substances, for example, casein, gum tragacanth, carboxymethyl cellulose and polyvinyl alcohol; and effect-promoting agents.

The compounds of the present invention can, if desired, be applied with other agricultural chemicals such as insecticides, acaricides, nematocides, antiviral agents, herbicides, plant-growth regulators and attractants (which classes of compounds include certain phosphoric acid esters, carbamates, dithio or thiol carbamates, chlorinated organic compounds, dinitro compounds, organosulfur and organometallic compounds, antibiotics, substituted diphenyl ethers, ureas and triazines), as well as with fertilizers.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20%, preferably 0.001–10%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.001–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects, acarids and nematodes, which comprises applying to at least one of correspondingly (a) such insects, (b) such acarids, (c) such nematodes and (d) the corresponding habitat thereof, i.e. the locus to be protected, a correspondingly combative or toxic amount, i.e., an insecticidally, acaricidally or nematocidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1 a) 200 ml of dioxane were added to a solution of 29 g of potassium hydroxide in 200 ml of water, and 64 g of O-(4-chlorophenyl)-N-methyl-amido-thionophosphoric acid chloride were added dropwise to the resulting solution, with agitation thereof, at room temperature. After completion of the addition, the mixture was stirred at 60°C for 1 hour. Water and dioxane were distilled off under reduced pressure, and water and benzene were added to the residue. Water was removed under reduced pressure from the resulting aqueous layer, and the residue was dissolved in acetone to separate the inorganic salt. The inorganic salt was removed by filtration and the acetone was distilled off. There were obtained 61 g of potassium O-(4-chlorophenyl)-N-methyl-amido-thiophosphate of the following formula:

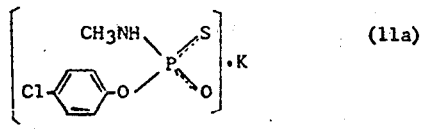 (11a)

b. 28 g of potassium O-(4-chlorophenyl)-N-methyl-amido-thiophosphate were dissolved in 100 ml of alcohol, and 15 g of 2 -methoxy-ethyl bromide were added to the solution at room temperature. Then the mixture was heated at 70°–80°C for 3 hours, with agitation thereof. After completion of the reaction, the alcohol was distilled off and benzene was added to the residue, following which the mixture was washed with water and 1% potassium carbonate solution. Then the mixture was dried over anhydrous sodium sulfate, and the benzene was distilled off. There were obtained 25 g, as a colorless oil, of O-(4-chlorophenyl)-S-(2-methoxyethyl)-N-methyl-thiolphosphoric acid ester amide of the following formula:

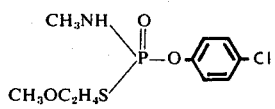 (11)

EXAMPLE 2

150 ml of dioxane were added to a solution of 12 g of potassium hydroxide in 50 ml of water, and 30 g of O-(4-methylthiophenyl)-N-isopropyl-amido-thionophosphoric acid chloride were added dropwise to the solution at 30°–40°C, with agitation thereof. After completion of the addition, the mixture was stirred for 1 hour at 60°C and 15.5 g of 2-ethoxyethyl bromide was added dropwise to the mixture. Then the mixture was stirred at 70°–80°C for 3 hours. Dioxane was removed from the mixture by distillation and benzene was added to the residue. The mixture was washed with water and 1% potassium carbonate solution and then dried over anhydrous sodium sulfate. Benzene was distilled off, and the residue was recrystallized from a mixture of benzene and n-hexane. There were obtained 28 g, in the form of white crystals, of O-(4-methylthiophenyl-S-(2-ethoxyethyl)-N-isopropyl-thiolphosphoric acid ester amide of the following formula

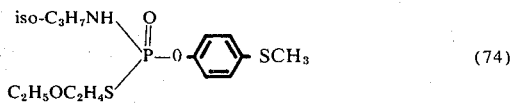 (74)

The product has a melting point of 82°–83.5°C. These and other typical compounds of this invention, which were synthesized by analogous methods are set forth in the following Table.

Table 1

| Compound No. | R¹ | R² | X | Physical Properties |
| --- | --- | --- | --- | --- |
| 1 | $CH_3$ | $CH_3$ | phenyl | b.p. 161 – 163°C/0.12 mmHg $n_D^{20}$ 1.5444 |
| 2 | $CH_3$ | $C_2H_5$ | phenyl | b.p. 155 – 158°C/0.07 mmHg $n_D^{20}$ 1.5350 |
| 3 | $CH_3$ | $n-C_3H_7$ | phenyl | b.p. 155 – 160°C/0.1 mmHg $n_D^{20}$ 1.5266 |
| 4 | $CH_3$ | $iso-C_3H_7$ | phenyl | b.p. 169 – 173°C/0.15 mmHg $n_D^{20}$ 1.5237 |
| 5 | $iso-C_3H_7$ | $CH_3$ | phenyl | b.p. 160 – 165°C/0.05 mmHg m.p. 43.5 – 45°C |
| 6 | $iso-C_3H_7$ | $C_2H_5$ | phenyl | b.p. 150 – 153°C/0.05 mmHg m.p. 50 – 51°C |
| 7 | $iso-C_3H_7$ | $n-C_3H_7$ | phenyl | b.p. 160 – 162°C/0.1 mmHg $n_D^{20}$ 1.5187 |
| 8 | $iso-C_3H_7$ | $iso-C_3H_7$ | phenyl | b.p. 168 – 172°C/0.1 mmHg m.p. 55 – 57°C |
| 9 | $iso-C_3H_7$ | $n-C_4H_9$ | phenyl | b.p. 165 – 170°C/0.08 mmHg $n_D^{20}$ 1.5125 |
| 10 | H | $C_2H_5$ | 4-Cl-phenyl | m.p. 67.5 – 70.5°C |
| 11 | $CH_3$ | $CH_3$ | 4-Cl-phenyl | b.p. 180 – 183°C/0.19 mmHg $n_D^{20}$ 1.5503 |

Table 1-continued

| Compound No. | R¹ | R² | X | Physical Properties |
|---|---|---|---|---|
| 12 | $CH_3$ | $C_2H_5$ | 4-Cl-C₆H₄- | b.p. 164 – 165°C/0.08 mmHg<br>$n_D^{20}$ 1.5428 |
| 13 | $CH_3$ | $n$-$C_3H_7$ | 4-Cl-C₆H₄- | b.p. 165 – 170°C/0.15 mmHg<br>$n_D^{20}$ 1.5263 |
| 14 | $CH_3$ | iso-$C_3H_7$ | 4-Cl-C₆H₄- | b.p. 175 – 179°C/0.1 mmHg<br>$n_D^{20}$ 1.5242 |
| 15 | iso-$C_3H_7$ | $C_2H_5$ | 4-Cl-C₆H₄- | b.p. 152 – 153°C/0.04 mmHg<br>m.p. 57 – 58°C |
| 16 | sec-$C_4H_9$ | $C_2H_5$ | 4-Cl-C₆H₄- | b.p. 180 – 185°C/0.2 mmHg<br>$n_D^{20}$ 1.5274 |
| 17 | iso-$C_3H_7$ | $C_2H_5$ | 2-Cl-C₆H₄- | b.p. 140 – 145°C/0.05 mmHg<br>$n_D^{20}$ 1.5190 |
| 18 | iso-$C_3H_7$ | $C_2H_5$ | 3-Cl-C₆H₄- | b.p. 155 – 160°C/0.1 mmHg<br>$n_D^{20}$ 1.5202 |
| 19 | H | $C_2H_5$ | 2,4-Cl₂-C₆H₃- | $n_D^{20}$ 1.5608 |
| 20 | $CH_3$ | $CH_3$ | 2,4-Cl₂-C₆H₃- | b.p. 178 – 183°C/0.15 mmHg<br>$n_D^{20}$ 1.5602 |
| 21 | $CH_3$ | $C_2H_5$ | 2,4-Cl₂-C₆H₃- | b.p. 170 – 172°C/0.08 mmHg<br>$n_D^{20}$ 1.5502 |
| 22 | $C_2H_5$ | $C_2H_5$ | 2,4-Cl₂-C₆H₃- | b.p. 165 – 173°C/0.15 mmHg<br>$n_D^{20}$ 1.5448 |
| 23 | iso-$C_3H_7$ | $CH_3$ | 2,4-Cl₂-C₆H₃- | b.p. 171 – 175°C/0.15 mmHg<br>$n_D^{20}$ 1.5402 |
| 24 | iso-$C_3H_7$ | $C_2H_5$ | 2,4-Cl₂-C₆H₃- | b.p. 168 – 174°C/0.1 mmHg<br>m.p. 42.5 – 43.5°C |
| 25 | iso-$C_3H_7$ | $n$-$C_3H_7$ | 2,4-Cl₂-C₆H₃- | b.p. 166 – 171°C/0.1 mmHg<br>$n_D^{20}$ 1.5327 |
| 26 | iso-$C_3H_7$ | iso-$C_3H_7$ | 2,4-Cl₂-C₆H₃- | b.p. 171 – 173°C/0.1 mmHg<br>$n_D^{20}$ 1.5301 |
| 27 | iso-$C_3H_7$ | $n$-$C_4H_9$ | 2,4-Cl₂-C₆H₃- | b.p. 173 – 177°C/0.1 mmHg<br>$n_D^{20}$ 1.5297 |
| 28 | sec-$C_4H_9$ | $C_2H_5$ | 2,4-Cl₂-C₆H₃- | b.p. 178 – 183°C/0.2 mmHg<br>$n_D^{20}$ 1.5390 |

Table 1-continued

| Compound No. | R¹ | R² | X | Physical Properties |
|---|---|---|---|---|
| 29 | iso-C₃H₇ | C₂H₅ | 2,6-Cl₂-C₆H₃ | b.p. 169 – 172°C/0.1 mmHg  $n_D^{20}$ 1.5315 |
| 30 | CH₃ | C₂H₅ | 2,4,5-Cl₃-C₆H₂ | b.p. 199 – 200°C/0.3 mmHg  $n_D^{20}$ 1.5618 |
| 31 | iso-C₃H₇ | C₂H₅ | 2,4,5-Cl₃-C₆H₂ | b.p. 171 – 172°C/0.05 mmHg  m.p. 78 – 80°C |
| 32 | C₂H₅ | C₂H₅ | 2,4,6-Cl₃-C₆H₂ | b.p. 165 – 170°C/0.15 mmHg  $n_D^{20}$ 1.5550 |
| 33 | iso-C₃H₇ | C₂H₅ | 2,4,6-Cl₃-C₆H₂ | b.p. 151 – 157°C/0.1 mmHg  m.p. 69 – 72°C |
| 34 | CH₃ | C₂H₅ | 4-Br-C₆H₄ | b.p. 182 – 188°C/0.2 mmHg  $n_D^{20}$ 1.5541 |
| 35 | iso-C₃H₇ | C₂H₅ | 4-Br-C₆H₄ | b.p. 171 – 174°C/0.1 mmHg  m.p. 64.5 – 66°C |
| 36 | iso-C₃H₇ | C₂H₅ | 2-CH₃-C₆H₄ | b.p. 166 – 169°C/0.15 mmHg  $n_D^{20}$ 1.5204 |
| 37 | iso-C₃H₇ | C₂H₅ | 3-CH₃-C₆H₄ | b.p. 170 – 174°C/0.15 mmHg  $n_D^{20}$ 1.5190 |
| 38 | iso-C₃H₇ | C₂H₅ | 4-CH₃-C₆H₄ | b.p. 161 – 168°C/0.15 mmHg  $n_D^{20}$ 1.5221 |
| 39 | H | C₂H₅ | 2-iso-C₃H₇-C₆H₄ | $n_D^{20}$ 1.5311 |
| 40 | CH₃ | C₂H₅ | 2-iso-C₃H₇-C₆H₄ | b.p. 166 – 169°C/0.08 mmHg  $n_D^{20}$ 1.5278 |
| 41 | iso-C₃H₇ | C₂H₅ | 2-iso-C₃H₇-C₆H₄ | b.p. 160 – 166°C/0.1 mmHg  $n_{D20}$ 1.5170 |
| 42 | H | C₂H₅ | 4-tert-C₄H₉-C₆H₄ | m.p. 53 – 54°C |
| 43 | CH₃ | C₂H₅ | 4-tert-C₄H₉-C₆H₄ | b.p. 173 – 174°C/0.08 mmHg  $n_D^{20}$ 1.5250 |
| 44 | iso-C₃H₇ | CH₃ | 4-tert-C₄H₉-C₆H₄ | b.p. 177 – 181°C/0.2 mmHg  $n_D^{20}$ 1.5211 |

Table 1-continued

| Compound No. | R¹ | R² | X | Physical Properties |
|---|---|---|---|---|
| 45 | iso-C₃H₇ | C₂H₅ | ⟨C₆H₄⟩-C₄H₉-tert | b.p. 184 – 189°C/0.15 mmHg<br>$n_D^{20}$ 1.5159 |
| 46 | iso-C₃H₇ | n-C₃H₇ | ⟨C₆H₄⟩-C₄H₉-tert | b.p. 173 – 178°C/0.1 mmHg<br>$n_D^{20}$ 1.5109 |
| 47 | iso-C₃H₇ | iso-C₃H₇ | ⟨C₆H₄⟩-C₄H₉-tert | b.p. 175 – 177°C/0.1 mmHg |
| 48 | iso-C₃H₇ | n-C₄H₉ | ⟨C₆H₄⟩-C₄H₉-tert | b.p. 166 – 170°C/0.1 mmHg<br>$n_D^{20}$ 1.5104 |
| 49 | n-C₄H₉ | C₂H₅ | ⟨C₆H₄⟩-C₄H₉-tert | b.p. 178 – 183°C/0.1 mmHg<br>$n_D^{20}$ 1.5150 |
| 50 | sec-C₄H₉ | C₂H₅ | ⟨C₆H₄⟩-C₄H₉-tert | b.p. 179 – 182°C/0.1 mmHg<br>$n_D^{20}$ 1.5142 |
| 51 | CH₃ | C₂H₅ | 2,3-(CH₃)₂-C₆H₃ | b.p. 164 – 170°C/0.1 mmHg<br>$n_D^{20}$ 1.5323 |
| 52 | iso-C₃H₇ | C₂H₅ | 2,3-(CH₃)₂-C₆H₃ | b.p. 160 – 162°C/0.05 mmHg<br>$n_D^{20}$ 1.5218 |
| 53 | CH₃ | C₂H₅ | 2,6-(CH₃)₂-C₆H₃ | b.p. 174 – 177°C/0.15 mmHg<br>$n_D^{20}$ 1.5352 |
| 54 | iso-C₃H₇ | C₂H₅ | 2,6-(CH₃)₂-C₆H₃ | b.p. 160 – 165°C/0.05 mmHg<br>$n_D^{20}$ 1.5247 |
| 55 | CH₃ | C₂H₅ | 2,5-(CH₃)₂-C₆H₃ | b.p. 169 – 170°C/0.1 mmHg<br>$n_D^{20}$ 1.5322 |
| 56 | iso-C₃H₇ | C₂H₅ | 2,5-(CH₃)₂-C₆H₃ | b.p. 167 – 170°C/0.25 mmHg<br>$n_D^{20}$ 1.5201 |
| 57 | CH₃ | C₂H₅ | 3-iso-C₃H₇-4-CH₃-C₆H₃ | b.p. 160 – 166°C/0.07 mmHg<br>$n_D^{20}$ 1.5259 |
| 58 | iso-C₃H₇ | C₂H₅ | 3-iso-C₃H₇-4-CH₃-C₆H₃ | b.p. 173 – 178°C/0.2 mmHg<br>$n_D^{20}$ 1.5165 |
| 59 | iso-C₃H₇ | C₂H₅ | 2-CH₃-3-Cl-C₆H₃ | b.p. 188 – 192°C/0.12 mmHg<br>$n_D^{20}$ 1.5313 |
| 60 | iso-C₃H₇ | C₂H₅ | 2-Cl-5-CH₃-C₆H₃ | b.p. 181 – 184°C/0.12 mmHg<br>$n_D^{20}$ 1.5334 |

Table 1-continued

| Compound No. | R¹ | R² | X | Physical Properties |
|---|---|---|---|---|
| 61 | iso-$C_3H_7$ | $C_2H_5$ |  | b.p. 189 – 192°C/0.15 mmHg  $n_D^{20}$ 1.5322 |
| 62 | sec-$C_4H_9$ | $C_2H_5$ |  | b.p. 190 – 194°C/0.2 mmHg  $n_D^{20}$ 1.5308 |
| 63 | iso-$C_3H_7$ | $C_2H_5$ |  | b.p. 187 – 192°C/0.2 mmHg  $n_D^{20}$ 1.5291 |
| 64 | $CH_3$ | $C_2H_5$ | 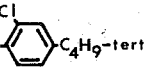 | b.p. 184 – 187°C/0.3 mmHg  $n_D^{20}$ 1.5329 |
| 65 | iso-$C_3H_7$ | $C_2H_5$ | 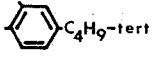 | b.p. 170 – 175°C/0.06 mmHg  $n_D^{20}$ 1.5229 |
| 66 | $CH_3$ | $C_2H_5$ | 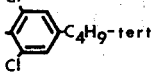 | b.p. 191 – 195°C/0.08 mmHg  $n_D^{20}$ 1.5429 |
| 67 | $CH_3$ | $C_2H_5$ | 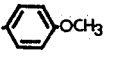 | b.p. 181 – 185°C/0.1 mmHg  $n_D^{20}$ 1.5380 |
| 68 | iso-$C_3H_7$ | $C_2H_5$ | 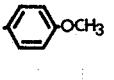 | b.p. 175 – 181°C/0.15 mmHg  m.p. 49.5 – 50.5°C |
| 69 | $CH_3$ | $C_2H_5$ |  | b.p. 183 – 186°C/0.1 mmHg  $n_D^{20}$ 1.5401 |
| 70 | iso-$C_3H_7$ | $C_2H_5$ |  | b.p. 168 – 173°C/0.15 mmHg  $n_D^{20}$ 1.5259 |
| 71 | $CH_3$ | $C_2H_5$ |  | b.p. 156 – 160°C/0.08 mmHg  $n_D^{20}$ 1.5261 |
| 72 | iso-$C_3H_7$ | $C_2H_5$ |  | b.p. 166 – 168°C/0.1 mmHg  $n_D^{20}$ 1.5157 |
| 73 | $CH_3$ | $C_2H_5$ | 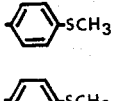 | b.p. 180 – 185°C/0.07 mmHg  m.p. 53.5 – 55°C |
| 74 | iso-$C_3H_7$ | $C_2H_5$ | 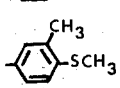 | m.p. 82 – 83.5°C |
| 75 | $CH_3$ | $C_2H_5$ |  | b.p. 202 – 204°C/0.2 mmHg  $n_D^{20}$ 1.5681 |

Table 1-continued

| Compound No. | R¹ | R² | X | Physical Properties |
|---|---|---|---|---|
| 76 | iso-C$_3$H$_7$ | CH$_3$ | 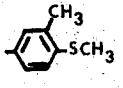 | b.p. 192 – 197°C/0.2 mmHg<br>$n_D^{20}$ 1.5608 |
| 77 | iso-C$_3$H$_7$ | C$_2$H$_5$ | 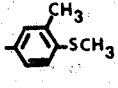 | b.p. 190 – 195°C/0.1 mmHg<br>m.p. 62 – 63.5°C |
| 78 | iso-C$_3$H$_7$ | n-C$_4$H$_9$ | 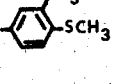 | b.p. 198 – 202°C/0.15 mmHg<br>$n_D^{20}$ 1.5447 |
| 79 | iso-C$_3$H$_7$ | C$_2$H$_5$ | 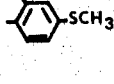 | b.p. 193 – 195°C/0.1 mmHg |
| 80 | iso-C$_3$H$_7$ | C$_2$H$_5$ | 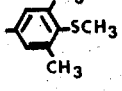 | b.p. 188 – 193°C/0.05 mmHg |
| 81 | CH$_3$ | C$_2$H$_5$ | 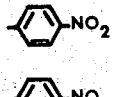 | $n_D^{20}$ 1.5560 |
| 82 | iso-C$_3$H$_7$ | C$_2$H$_5$ | 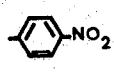 | m.p. 52.5 – 54°C |
| 83 | sec-C$_4$H$_9$ | C$_2$H$_5$ | 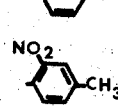 | $n_D^{20}$ 1.5317 |
| 84 | CH$_3$ | C$_2$H$_5$ | 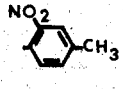 | $n_D^{20}$ 1.5400 |
| 85 | CH$_3$ | C$_2$H$_5$ | 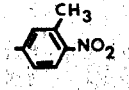 | $n_D^{20}$ 1.5470 |
| 86 | iso-C$_3$H$_7$ | C$_2$H$_5$ | 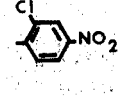 | b.p. 175 – 180°C/0.15 mmHg<br>$n_D^{20}$ 1.5351 |
| 87 | iso-C$_3$H$_7$ | C$_2$H$_5$ | 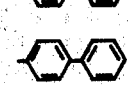 | $n_D^{20}$ 1.5389 |
| 88 | iso-C$_3$H$_7$ | C$_2$H$_5$ | 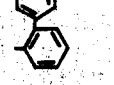 | $n_D^{20}$ 1.5526 |
| 89 | CH$_3$ | C$_2$H$_5$ |  | b.p. 220 – 225°C/0.2 mmHg<br>m.p. 64.5 – 66°C |
| 90 | iso-C$_3$H$_7$ | C$_2$H$_5$ |  | m.p. 99 – 100.5°C |
| 91 | CH$_3$ | C$_2$H$_5$ |  | b.p. 197 – 199°C/0.15 mmHg<br>m.p. 74 – 75.5°C |

Table 1-continued

| Compound No. | R¹ | R² | X | Physical Properties |
|---|---|---|---|---|
| 92 | iso-$C_3H_7$ | $CH_3$ |  | m.p. 91 – 93°C |
| 93 | iso-$C_3H_7$ | $C_2H_5$ |  | m.p. 79.5 – 81.5°C |
| 94 | iso-$C_3H_7$ | iso-$C_3H_7$ |  | m.p. 63 – 65.5°C |
| 95 | iso-$C_3H_7$ | n-$C_4H_9$ |  | b.p. 201 – 205°C/0.12 mmHg<br>m.p. 61 – 63°C |
| 96 | iso-$C_3H_7$ | $C_2H_5$ | 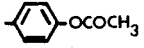 | b.p. 199 – 203°C/0.13 mmHg |
| 97 | $CH_3$ | $C_2H_5$ |  | b.p. 206 – 210°C/0.12 mmHg<br>$n_D^{20}$ 1.5913 |
| 98 | iso-$C_3H_7$ | $C_2H_5$ |  | b.p. 195 – 200°C/0.15 mmHg<br>$n_D^{20}$ 1.5749 |
| 99 | $CH_3$ | $C_2H_5$ |  | b.p. 207 – 212°C/0.19 mmHg<br>$n_D^{20}$ 1.5915 |
| 100 | iso-$C_3H_7$ | $C_2H_5$ |  | m.p. 63 – 65°C |

The compositions of the invention are illustrated in the following Examples, in which the active compounds are identified by the numbers assigned to them in Table 1 above. Parts are by weight.

EXAMPLE 3 (Wettable Powder)

15 parts of compound No. 55, 80 parts of a 1:5 mixture of diatomaceous earth and kaolin, and 5 parts of an emulsifier, Runnox (a polyoxyethylene alkylaryl ether) were ground and mixed together to form a wettable powder. It was diluted with water before actual application.

EXAMPLE 4 (Emulsifiable Liquor)

30 parts of compound No. 21, 30 parts of xylene, 30 parts of Kawakazol (a high boiling point hydrocarbon), and 10 parts of emulsifier, Sorpol (a polyoxyethylene alkylaryl ether), were mixed by stirring to form an emulsifiable liquor. It was diluted with water at 0.05% before being applied by spraying.

EXAMPLE 5 (Dust)

2 parts of compound No. 73 and 98 parts of a 1:3 mixture of talc and clay were ground and mixed together to form a dust. The dust was applied by scattering.

EXAMPLE 6 (Dust)

1.5 parts of compound No. 97, 2 parts of an organic phosphoric acid ester, 0.5 part of isopropyl hydrogen phosphate (PAP and 96 parts of a 1:3 mixture of talc and clay were ground and mixed together to form a dust. The dust was applied by scattering.

EXAMPLE 7 (Granules)

25 parts of water were added to a mixture of 10 parts of compound No. 24, 10 parts of bentonite, 78 parts of a 1:3 mixture of talc and clay and 2 parts of lignin sulfonate. The mixture was intimately blended and finely divided by means of an extruding granulator to obtain granules of 20–40 mesh, followed by drying at 40°–50°C. The resulting granules were applied by spraying.

EXAMPLE 8 (Granules)

95 parts of clay particles of a size distribution of 0.2–2mm were placed in a rotary mixer and a solution of 5 parts of compound No. 14 in an organic solvent was sprayed onto the particles being rotated, thereby wetting them homogeneously. Then they were dried at 40°–50°C to form coated granules; these were applied by spraying.

EXAMPLE 9 (Oil Preparation)

0.5 part of compound No. 34, 20 parts of Velsicol (a high boiling point aromatic hydrocarbon), and 79.5 parts of Deobase (deodorized kerosine) were mixed by stirring to form an oil preparation. The preparation was applied by spraying.

The pesticidal activity of the compounds of this invention is illustrated in the following test Examples.

EXAMPLE 10

Test on effects against *Prodenia litura* larvae:

Preparation of Sample Formulation:

Solvent: 3 parts by weight of dimethyl formamide
Emulsifier: 0.1 part by weight of alkylaryl polyglycol ether In order to prepare a suitable formulation of an active compound, one part by weight of the active compound is mixed with the above amount of the solvent containing the above amount of the emulsifier, and the mixture is diluted with water to form an aqueous formulation containing the active compound at a prescribed concentration.

Test Procedure:

Sweet potato leaves are dipped in a formulation containing the active compound at the prescribed concentration, and they are then dried in air and placed in a 9 cm diameter Petri dish. Then 10 third-instar cotton-worm (*Prodenia litura*) larvae are put into the dish, which is kept in a thermostat chamber maintained at 28°C. After 24 hours have passed, the number of dead larvae is counted and the killing ratio is calculated. Results are shown in Table 2.

Table 2

| Compound No. | Effects against cotton-worm larvae Killing Ratio Active ingredient concentration | | |
|---|---|---|---|
| | 1000 ppm | 300 ppm | 100 ppm |
| 3 | 100 | 80 | 40 |
| 4 | 100 | 100 | 50 |
| 11 | 100 | 100 | 50 |
| 13 | 100 | 100 | 50 |
| 14 | 100 | 100 | 100 |
| 20 | 100 | 100 | 60 |
| 21 | 100 | 100 | 100 |
| 30 | 100 | 100 | 100 |
| 34 | 100 | 100 | 70 |
| 40 | 100 | 100 | 60 |
| 43 | 100 | 90 | 70 |
| 51 | 100 | 100 | 70 |
| 53 | 100 | 100 | 90 |
| 55 | 100 | 100 | 100 |
| 57 | 100 | 100 | 80 |
| 64 | 100 | 100 | 50 |
| 66 | 100 | 100 | 50 |
| 67 | 100 | 100 | 50 |
| 69 | 100 | 100 | 100 |
| 71 | 100 | 100 | 80 |
| 73 | 100 | 100 | 90 |
| 75 | 100 | 100 | 100 |
| 81 | 100 | 100 | 50 |

Table 2-continued

| Compound No. | Effects against cotton-worm larvae Killing Ratio Active ingredient concentration | | |
|---|---|---|---|
| | 1000 ppm | 300 ppm | 100 ppm |
| 85 | 100 | 100 | 50 |
| 89 | 100 | 100 | 80 |
| 91 | 100 | 100 | 90 |
| 97 | 100 | 100 | 100 |
| 99 | 100 | 100 | 95 |
| Sumithion | 100 | 90 | 20 |

Note:
Sumithion: O,O-dimethyl-O-(3-methyl-4-nitrophenyl) phosphorothioate, a commercially available comparison.

EXAMPLE 11

Test on effects against the two-spotted spider mite (*Tetranychus urticae*):

Test Procedure

Haricot plants having two developing leaves and planted in 6 cm diameter pots are infected with, per pot, 50–100 imagines and nymphs of the two-spotted spider mite. Two days after infestation, an aqueous formulation (prepared in the manner as described in Example 10) containing the active compound at a prescribed concentration is sprayed in an amount of 40 ml per pot. The pot is kept in a greenhouse for 10 days and the control effect is evaluated. The evaluation is expressed as an index on the following scale:

Index

3: No living imago, nymph or egg
2: less than 5% of living imagines, nymphs and eggs, based on the untreated control
1: 5 – 50% of living imagines, nymphs and eggs, based on the untreated control. The results are shown in Table 3.

Table 3

| Compound No. | Effects against the two-spotted spider mite Control effect index | |
|---|---|---|
| | 300 ppm | 100 ppm |
| 1 | 3 | 3 |
| 2 | 3 | 2 |
| 3 | 3 | 3 |
| 4 | 3 | 3 |
| 5 | 3 | 3 |
| 6 | 3 | 3 |
| 7 | 3 | 2 |
| 8 | 3 | 2 |
| 9 | 3 | 3 |
| 10 | 3 | 3 |
| 11 | 3 | 3 |
| 12 | 3 | 3 |
| 13 | 3 | 3 |
| 14 | 3 | 3 |
| 15 | 3 | 3 |
| 16 | 3 | 3 |
| 17 | 3 | 3 |
| 18 | 3 | 3 |
| 19 | 3 | 3 |
| 20 | 3 | 3 |
| 21 | 3 | 3 |
| 22 | 3 | 3 |
| 23 | 3 | 3 |
| 24 | 3 | 3 |
| 25 | 3 | 3 |
| 26 | 3 | 3 |
| 27 | 3 | 3 |
| 28 | 3 | 3 |
| 29 | 3 | 3 |
| 30 | 3 | 3 |
| 31 | 3 | 3 |
| 32 | 3 | 3 |
| 33 | 3 | 1 |
| 34 | 3 | 3 |
| 35 | 3 | 3 |
| 36 | 3 | 2 |

Table 3-continued

Effects against the two-spotted spider mite
Control effect index

| Compound No. | 300 ppm | 100 ppm |
| --- | --- | --- |
| 37 | 3 | 1 |
| 38 | 3 | 1 |
| 39 | 3 | 3 |
| 40 | 3 | 3 |
| 41 | 3 | 3 |
| 42 | 3 | 3 |
| 43 | 3 | 3 |
| 44 | 3 | 3 |
| 45 | 3 | 3 |
| 46 | 3 | 3 |
| 47 | 3 | 2 |
| 48 | 3 | 2 |
| 49 | 3 | 3 |
| 50 | 3 | 3 |
| 51 | 3 | 3 |
| 52 | 3 | 3 |
| 53 | 3 | 3 |
| 54 | 2 | 1 |
| 55 | 3 | 3 |
| 56 | 3 | 3 |
| 57 | 3 | 3 |
| 58 | 3 | 2 |
| 59 | 3 | 3 |
| 60 | 3 | 3 |
| 61 | 3 | 3 |
| 62 | 3 | 2 |
| 63 | 3 | 1 |
| 64 | 3 | 3 |
| 65 | 3 | 3 |
| 66 | 3 | 3 |
| 67 | 3 | 3 |
| 68 | 3 | 2 |
| 69 | 3 | 3 |
| 70 | 3 | 3 |
| 71 | 3 | 3 |
| 72 | 3 | 3 |
| 73 | 3 | 3 |
| 74 | 3 | 3 |
| 75 | 3 | 3 |
| 76 | 3 | 1 |
| 77 | 3 | 2 |
| 78 | 3 | 1 |
| 79 | 3 | 3 |
| 80 | 3 | 2 |
| 81 | 3 | 3 |
| 82 | 3 | 3 |
| 83 | 3 | 3 |
| 84 | 3 | 3 |
| 85 | 3 | 3 |
| 86 | 2 | 1 |
| 87 | 3 | 1 |
| 88 | 3 | 2 |
| 89 | 3 | 3 |
| 90 | 2 | 1 |
| 91 | 3 | 3 |
| 92 | 3 | 2 |
| 93 | 3 | 2 |
| 94 | 3 | 3 |
| 95 | 3 | 3 |
| 96 | 3 | 1 |
| 97 | 3 | 3 |
| 98 | 3 | 3 |
| 99 | 3 | 3 |
| 100 | 2 | 1 |
| Galecron | 2 | 0 |

Note:
Galecron: N'-(2-methyl-4-chlorophenyl)-N,N-dimethyl formamizine hydrochloride, a commercially available comparison.

EXAMPLE 12

Test on effects against root knot nematode (*Meloidogyne incognita acrita*):

Preparation of Simple Formulation 2 parts by weight of the active compound are mixed with 98 parts by weight of talc, and the mixture is ground to form a dust.

Test Procedure

The so prepared formulation is mixed with soil, tained with sweet-potato root knot nematodes, in an amount such that a prescribed concentration of the active compound is attained in the soil. The treated soil is stirred and mixed until uniform, and then it is packed into pots each having an area of 1/5000 are. About 20 tomato seeds (Kurihara variety) are sowed per pot and cultivated for 4 weeks in a greenhouse. Then each root is drawn out from the soil without damaging it. The degree of damage caused by the nematodes is evaluated with respect to 10 roots as one group based on the following scale:

Damage Degree

0: no knot (perfect control)
1: knots are formed to a slight extent
2: knots are formed to a moderate extent
3: knots are formed to a considerable extent
4: formation of knots is extreme (the same as in the untreated control).

The root-knot index is determined by the following equation:

$$\text{Root-Knot Index} = \frac{\Sigma \text{ (rank value)} \times \text{(rank population)}}{\text{(whole populaton)} \times 4} \times 100\%$$

The results are shown in Table 4

Table 4

Results of test on effects against the root-knot nematode

| Compound No. | Active ingredient concentration (ppm) | Root knot index (%) |
| --- | --- | --- |
| 21 | 30/ 0 | |
|  | 15 | 1.7 |
| 24 | 30 | 0 |
|  | 15 | 1.7 |
| 34 | 30 | 0 |
|  | 15 | 3.1 |
| 73 | 30 | 0 |
|  | 15 | 0.2 |
| 74 | 30 | 0 |
|  | 15 | 0.3 |
| 77 | 30 | 0 |
|  | 15 | 1.1 |
| VC | 30 | 0.8 |
|  | 15 | 25.0 |

Note:
VC: diethyldichlorophenyl-thiophosphate, a commercially available comparison.

It will be appreciated that the instant specification and examples are set forth by way of illustration and not limitation, and that various modifications and changes may be made without departing from the spirit and scope of the present invention.

What is claimed is:

1. An O-aryl-S-alkoxy-ethyl-thiolphosphoric acid ester amide of the formula

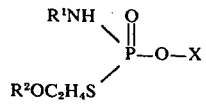

in which
R$^1$ is hydrogen or lower alkyl,
R$^2$ is lower alkyl, and
X is a group of the formula

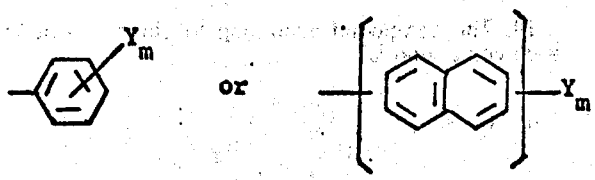

in which
 m is 1, 2 or 3, and
 each Y independently is lower alkoxy, lower alkylmercapto or lower alkoxycarbonyl.

2. The compound according to claim 1 wherein such compound is O-(2-methoxyphenyl)-S-(2-ethoxyethyl)-N-methyl-thiolphosphoric acid ester amide of the formula

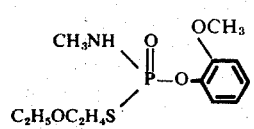

3. The compound according to claim 1 wherein such compound is 0-(4-methylmercaptophenyl)-S-(2-ethoxy-ethyl)-N-methyl-thiolphosphoric acid ester amide of the formula

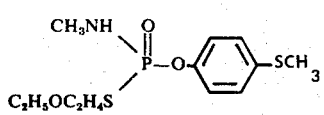

4. An O-aryl-S-alkoxy-ethyl-thiolphosphoric acid ester amide selected from the group consisting of

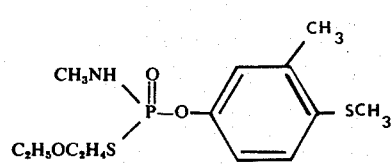

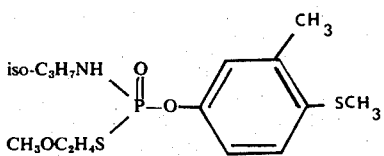

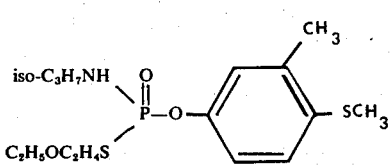

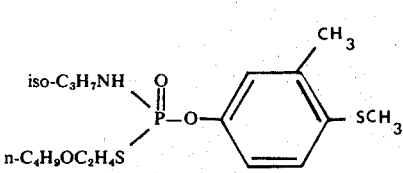

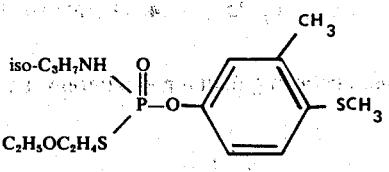

5. The compound according to claim 4, wherein such compound is

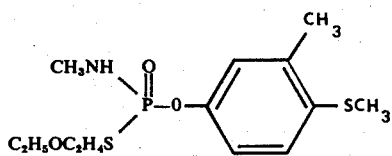

6. The compound according to claim 4, wherein such compound is

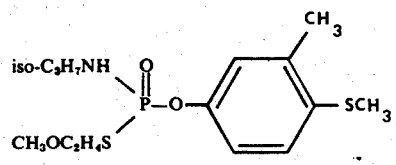

7. The compound according to claim 4, wherein such compound is

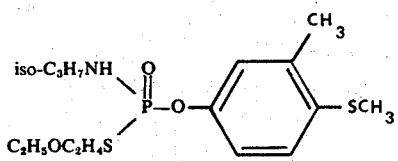

8. The compound according to claim 4, wherein such compound is

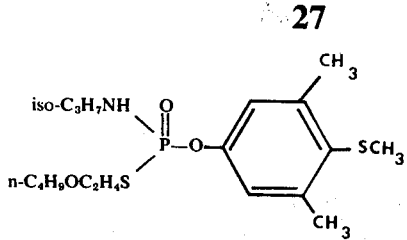
9. The compound according to claim 4, wherein such compound is
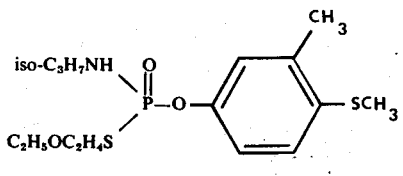
10. The compound according to claim 4, wherein such compound is
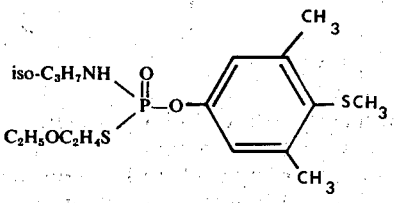
* * * * *

UNITED STATES PATENT AND TRADEMARK OFFICE
CERTIFICATE OF CORRECTION

PATENT NO. : 3,970,723

DATED : July 20, 1976

INVENTOR(S) : Shigeo Kishino et al

It is certified that error appears in the above-identified patent and that said Letters Patent are hereby corrected as shown below:

| | |
|---|---|
| Col. 24, line 35 | cancel "30/0" in second column and substitute -- 30 -- |
| Col. 24, line 35 | in third column, insert -- 0 -- |
| Col. 24, line 35 | in third column, cancel "0.3" and substitute -- 0.8 -- |
| Claim 4, col. 26, line 10 | cancel "$CH_3$" on upper left of hexagon and substitute -- $CH_3$ -- on <u>upper right</u> of hexagon |
| Claim 8, col. 27, line 8 | delete "$CH_3$" at lower right of hexagon |
| Claim 9, col. 27, line 14 | cancel "$CH_3$" on upper right of hexagon and substitute --$CH_3$-- on <u>upper left</u> of hexagon |

UNITED STATES PATENT OFFICE

CERTIFICATE OF CORRECTION

Patent No. 3,970,728   Dated July 20, 1976

Inventor(s) Shigeo Kishino et al.

It is certified that error appears in the above-identified patent and that said Letters Patent are hereby corrected as shown below:

on <u>upper left</u> of hexagon.

Signed and Sealed this

Sixth Day of September 1977

[SEAL]

Attest:

RUTH C. MASON　　　　LUTRELLE F. PARKER
*Attesting Officer*　　*Acting Commissioner of Patents and Trademarks*